(12) United States Patent  
Raffai et al.

(10) Patent No.: US 7,960,606 B2  
(45) Date of Patent: Jun. 14, 2011

(54) MOUSE MODEL OF CHRONIC HEART FAILURE AND CORONARY ATHEROSCLEROSIS REGRESSION

(75) Inventors: Robert L. Raffai, Half Moon Bay, CA (US); Karl Weisgraber, Walnut Creek, CA (US)

(73) Assignees: The J. David Gladstone Institutes, Irvine, CA (US); The Regents of the University of California, Oakland, CA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 11/765,408

(22) Filed: Jun. 19, 2007

(65) Prior Publication Data

US 2008/0075663 A1 Mar. 27, 2008

Related U.S. Application Data

(60) Provisional application No. 60/805,311, filed on Jun. 20, 2006.

(51) Int. Cl.
*A01K 67/00* (2006.01)
*A01K 67/027* (2006.01)
*C12N 15/00* (2006.01)
*G01N 33/00* (2006.01)

(52) U.S. Cl. .............. 800/9; 800/18; 800/21; 800/22; 800/3

(58) Field of Classification Search .............. 800/9, 3, 800/18, 21, 22
See application file for complete search history.

(56) References Cited

U.S. PATENT DOCUMENTS

| | | | |
|---|---|---|---|
| 3,625,214 | A | 12/1971 | Higuchi et al. |
| 4,789,734 | A | 12/1988 | Pierschbacher |
| 4,906,474 | A | 3/1990 | Langer et al. |
| 4,925,673 | A | 5/1990 | Steiner et al. |
| 6,437,215 | B1 | 8/2002 | Krieger et al. |
| 2002/0108131 | A1* | 8/2002 | Krieger et al. ............ 800/3 |
| 2002/0194628 | A1 | 12/2002 | Weisgraber et al. |
| 2005/0223420 | A1* | 10/2005 | Krieger et al. ............ 800/18 |

FOREIGN PATENT DOCUMENTS

| | | |
|---|---|---|
| WO | WO 02/074967 | 9/2002 |
| WO | WO 2005/011494 | 2/2005 |

OTHER PUBLICATIONS

Clark et al Nature Reviews: Genetics. 2003,. 825-833.*
Niemann et al Rev. Sci, Tech. Off. Int. Spiz. 2005, (24), 285-298.*
Wheeler Theriogeneology. 2001, (56), 1345-1369.*
Denning et al Cloning and Stem Cells, 2001, 3(4), 221-231.*
Yanagimach et al Molecular and Cellular Endocrinology, 2002, 187, 241-248.*
Oback and Wells Cloning and Stem Cells, 2002, 4, 169-174.*
Wolf et al Journal of Biotechnology 1998, 65: 99-110.*
Stice et al Therigeneology, 1998,49: 129-138.*
Wooddell et al, Biochem Biophys Res Commun. Aug. 19, 2005;334(1):117-27.*
Carmell MA Nat Struct Biol. 2003; 10(2): 91-92.*
Sigmund, C Arterioscler. Thromb. Vasc. Biol.2000, 1425-1429.*
Griffiths et al Microscopy Research and Technique 1998, 41: 344-358.*
Tailleux et al Trends Pharmacol Sci. 2003:24(10):530-4.*
Schoonjans et al Stem Cells, 2003; 21:90-97.*
Wolfer et al Trends in Neuroscience, 2002, 25 (7): 336-340.*
Gerlai, Trends Neurosci. 1996, 19(5):177-81.*
Holschneider et al. Int J Devl Neuroscience, 2000, 18: 615-618.*
Braun, et al., "Probucol prevents early coronary heart disease and death in the high-density lipoprotein receptor SR-BI/apolipoprotein E double knockout mouse", *Proc Natl Acad Sci.*, 100:7283-7288 (2003).
Braun, et al., "Loss of SR-BI expression leads to the early onset of occlusive atherosclerotic coronary artery disease, spontaneous myocardial infarctions, severe cardiac dysfunction, and premature death in apolipoprotein E-deficient mice", *Circ. Res.*, 90(3):270-6 (2002).
Caligiuri, et al., "Myocardial infarction mediated by endothelin receptor signaling in hypercholesterolemic mice", *Proc. Natl. Acad. Sci. U.S.A.*, 96(12):6920-4 (1999).
Clark and Whitelaw, "A future for transgenic livestock", *Nat Rev Genet.* Oct. 4(10):825-33) (2003).
Cooper, "Hepatic uptake of chylomicron remnants", *J Lipid Res*, 38(11):2173-2192 (1997). Dansky, et al., "T and B lymphocytes play a minor role in atherosclerotic plaque formation in the apolipoprotein E-deficient mouse", *Proc. Natl. Acad. Sci. U.S.A.*, 94(9):4642-6 (1997).
Dorsett and Tuschl, "siRNAs: applications in functional genomics and potential as therapeutics." *Nat Rev Drug Discov.*, 3(4):318-29 (2004).
Gao, et al., "Serial echocardiographic assessment of left ventricular dimensions and function after myocardial infarction in mice", *Cardiovasc. Res.*, 45(2):330-8 (2000).
Gardin, et al., "Echocardiographic assessment of left ventricular mass and systolic function in mice", *Circ. Res.*, 76(5):907-14 (1995).
Guo, et al., "Temporal Control of Cre Recombinase-mediated in Vitro DNA Recombination by Tet-on Gene Expression System", *Acta Biochimica et Biophysica Sinica*, 37(2):133-138 (2005).

(Continued)

*Primary Examiner* — Anoop Singh
(74) *Attorney, Agent, or Firm* — Pabst Patent Group LLP

(57) ABSTRACT

An animal model has been developed where the animals can survive myocardial infarctions caused by diet-induced coronary atherosclerosis, and live with chronic heart failure. This animal model is a result of reduced activity of scavenger receptor class BI (SR-BI) and ApoE and the inducible activity of the Mx1-Cre gene. In a preferred embodiment, the model is a result of crossbreeding two transgenic mouse lines: a knockout of SR-BI (SRBI$^{-/-}$) and an impaired ApoE expressor (Apoe$^{h/h}$) to generate a strain referred to as Apoe$^{h/h}$SRB1$^{-/-}$ mice, which is then crossbred to mice that carry the inducible Mx1-Cre transgene. The Apoe$^{h/h}$SRB1$^{-/-}$ mouse model is genetically modified, enabling the offspring to rapidly and permanently lower their high blood cholesterol levels caused by dietary challenge. The ability to rapidly and permanently lower blood cholesterol levels in these mice stops and may cause the regression of occlusive coronary atherosclerosis restoring blood flow to the heart, allowing the mice to survive from myocardial infarction and live with chronic heart failure.

4 Claims, 2 Drawing Sheets

OTHER PUBLICATIONS

Kemp, et al., "Elimination of background recombination: somatic induction of Cre by combined transcriptional regulation and hormone binding affinity.", Nucleic Acids Res. Jul. 1, 2004;32(11):e92. (2004).

Kocher, et al., "Targeted disruption of the PDZK1 gene in mice causes tissue-specific depletion of the high density lipoprotein receptor scavenger receptor class B type I and altered lipoprotein metabolism", *J Biol Chem* 278(52):52820-52825 (2003).

Kühn, "Inducible gene targeting in mice", *Science* 269 (5229):1427-1429 (1995).

Liao, et al., "Echocardiographic assessment of LV hypertrophy and function in aortic-banded mice: necropsy validation", *Am. J. Physiol. Heart Circ. Physiol.*, 282(5):H1703-8 (2002).

Mahley and Ji, "Remnant lipoprotein metabolism: key pathways involving cell-surface heparan sulfate proteoglycans and apolipoprotein E", *J Lipid Res*, 40:1-16 (1999).

Miettinen, et al., "Abnormal lipoprotein metabolism and reversible female infertility in HDL receptor (SR-BI)-deficient mice", *J Clin Invest.*, 108(11):1717-22 (2001).

Nieland, et al., "Discovery of chemical inhibitors of the selective transfer of lipids mediated by the HDL receptor SR-BI", *Proc Natl Acad Sci U S A*. 99(24):15422-7 (2002).

Niemann, et al., "Transgenic farm animals: Present and future", *Rev. Sci. Tech. Off. Int. Spiz.*, 24:285-298 (2005).

Nishimura, et al., "Autoimmune dilated cardiomyopathy in PD-1 receptor-deficient mice", *Science*, 291(5502):319-2 (2001).

Prelle, et al., "Pluripotent stem cells—model of embryonic development, tool for gene targeting, and basis of cell therapy", *Anat. Histol. Embryol.*, 31(3):169-86 (2002).

Raffai and Weisgraber, "Hypomorphic apolipoprotein E mice: a new model of conditional gene repair to examine apolipoprotein E-mediated metabolism", *J. Biol Chem.* 277(13)11064-11068 (2002).

Raffai, et al., "Introduction of human apolipoprotein E4 "domain interaction" into mouse apolipoprotein E", *Proc Natl Acad Sci USA*, 98(20):11587-11591 (2001).

Reardon, et al., "Effect of immune deficiency on lipoproteins and atherosclerosis in male apolipoprotein E-deficient mice", *Arterioscler. Thromb. Vasc. Biol.*, 21(6):1011-6 (2001).

Rigotti, et al., "The role of the high-density lipoprotein receptor SR-BI in the lipid metabolism of endocrine and other tissues", *Endocr Rev.*, 24(3):357-87 (2003).

Rigotti, et al., "A targeted mutation in the murine gene encoding the high density lipoprotein (HDL) receptor scavenger receptor class B type I reveals its key role in HDL metabolism", *Proc Natl Acad Sci USA*, 94:12610-12615 (1997).

Rohlmann, et al., "Inducible inactivation of hepatic LRP gene by cre-mediated recombination confirms role of LRP in clearance of chylomicron remnants", *J. Clin. Invest.*, 101: 689-695 (1998).

Roselaar, et al., "Lymphocyte populations in atherosclerotic lesions of apoE −/− and LDL receptor −/− mice. Decreasing density with disease progression", *Arterioscler. Thromb. Vasc. Biol.*, 16(8):1013-8 (1996).

Roth, et al., "Impact of anesthesia on cardiac function during echocardiography in mice", *Am. J. Physiol. Heart Circ. Physiol,.* 282(6):H2134-40 (2002).

Schneider, et al., "Differential, inducible gene targeting in renal epithelia, vascular endothelium, and viscera of Mx1Cre mice", *Am. J. Physiol. Renal Physiol.*, 284(2):F411-F417 (2002).

Tanaka, et al., "Transthoracic echocardiography in models of cardiac disease in the mouse", *Circulation*, 94(5):1109-17 (1996).

Takuma, et al., "Anesthetic inhibition in ischemic and nonischemic murine heart: comparison with conscious echocardiographic approach", *Am. J. Physiol. Heart Circ. Physiol.*, 280(5):H2364-70 (2001).

Van Eck, et al., "Differential effects of scavenger receptor BI deficiency on lipid metabolism in cells of the arterial wall and in the liver", *J Biol Chem*, 278(26):23699-23705 (2003).

Weisgraber, "Apolipoprotein E: structure-function relationships", *Adv Protein Chem.*, 45:249-302 (1994).

Wheeler, et al., "Transgenic technology and applications in swine", *Theriogenology*, 56(8):1345-69 (2001).

Yang, et al., "Echocardiographic assessment of cardiac function in conscious and anesthetized mice", *Am. J. Physiol.*, 277(5 Pt 2):H1967-74 (1999).

Zhang, et al., "Diet-induced occlusive coronary atherosclerosis, myocardial infarction, cardiac dysfunction, and premature death in scavenger receptor class B type I-deficient, hypomorphic apolipoprotein ER61 mice", *Circulation* 111(25):3457-64 (2005).

Zimmer and Gruss, "Production of chimaeric mice containing embryonic stem (ES) cells carrying a homoeobox Hox 1.1 allele by homologous recombination", *Nature*, 338(6211):150-3 (1989).

Zhang, et al., "Inactivation of macrophage scavenger receptor class B type I promotes atherosclerotic lesion development in apolipoprotein E-deficient mice", *Circulation*, 108(18):2258-63 (2003).

\* cited by examiner

- 2-5% of wildtype plasma apoE levels
- Display near normal plasma lipid levels
- Normal expression of apoE restored by Cre-recombination in Mx1-Cre mice

MOUSE MODEL OF CHRONIC HEART FAILURE AND CORONARY ATHEROSCLEROSIS REGRESSION

CROSS-REFERENCE TO RELATED APPLICATIONS

This application claims priority to U.S. Ser. No. 60/805,311 filed Jun. 20, 2006.

STATEMENT OF FEDERALLY SPONSORED SUPPORT

This invention was made with Government support under Grant No. AG020235, awarded by the National Institutes of Health. The Government has certain rights in this invention.

BACKGROUND OF THE INVENTION

This invention is generally in the area of a transgenic animal model that is characterized by chronic heart failure ("CHF") and which can survive an infarction caused by diet-induced coronary atherosclerosis. The animal model is useful to study CHF and treatments for chronic heart failure and coronary atherosclerosis regression.

Coronary atherosclerosis refers to the hardening and narrowing of the coronary arteries. The coronary arteries supply the blood that carries oxygen and nutrients to the heart muscle. When coronary arteries are narrowed or blocked by atherosclerosis, they cannot deliver an adequate amount of blood to the heart muscle. Disease caused by the lack of blood supply to heart muscle is called coronary heart disease (CHD). Coronary heart diseases is characterized by heart attacks, sudden unexpected death, chest pain, abnormal heart rhythms, and heart failure due to weakening of the heart muscle.

Chronic heart failure is the most common medical condition afflicting the western world. The major cause of CHF is myocardial infarction or the death of heart muscle during a heart attack, caused by coronary atherosclerosis. One of the risk factors for developing coronary atherosclerosis is elevated blood cholesterol. As blood cholesterol rises, so does risk of coronary heart disease and heart failure. When other risk factors (such as high blood pressure and tobacco smoke) are present, this risk increases even more. A person's cholesterol level is also affected by age, sex, heredity and diet. Cholesterol is vital for healthy cells. It is so important that the body does not rely on a dietary source, but produces its own cholesterol. However, if the body accumulates too much cholesterol, the cholesterol will deposit on the walls of arteries, which can damage or block the arteries, and cause a heart attack.

Excess cholesterol is produced when the diet is rich in saturated fats. An animal model for coronary heart disease (Apoe$^{h/h}$SRB1$^{-/-}$ mice) is described in Zhang, et al., Circulation 111(25):3457-64 (2005) and WO 2005/011494. Apoe$^{h/h}$ SRB1$^{-/-}$ mice have slightly elevated blood cholesterol levels when fed a normal low fat diet, but do not develop coronary atherosclerosis or heart disease. However, when fed a diet rich in fat and cholesterol, Apoe$^{h/h}$SRB1$^{-/-}$ mice develop very high blood cholesterol levels because of their low amounts of Arg61 apolipoproprotein E (ApoE) in the blood. High blood cholesterol levels rapidly cause occlusive coronary atherosclerosis in these mice, and they are subject to sudden death from severe heart failure caused by myocardial infarctions within 35 days of initiating the high cholesterol diet.

Myocardial infraction is currently treated by restoring blood flow in the heart by the placement of a drug eluting stent in the obstructed coronary artery or by coronary artery bypass surgery, alone or in combination with drugs that increase blood flow and inhibit platelet aggregation. However, despite restoration of blood flow, the heart remains damaged and, depending on the severity of the original heart attack, CHF results, resulting in reduced quality of life, including morbidity.

At the moment, there are very few technical solutions to significantly improve heart function in individuals with CHF. A major reason for the lack of treatments is the lack of reliable animal models that suffer from human-like CHF caused by myocardial infarction during a heart attack. A limitation of the coronary heart disease model described in WO 2005/011494 is the inability of the animals to recover from the coronary heart failure. Survival of the animals in WO 2005/011494 goes from 100% to 50%, ultimately reaching 0% by 45 days. An ideal animal model for CHF would be able to recover from myocardial infarctions caused by the blockage of coronary arteries by atherosclerosis, and develop the features characteristic of CHF. Such a model would provide a unique platform for scientists to develop new treatments for chronic heart failure in humans. Such a model would also be an ideal model for coronary atherosclerosis regression.

It is therefore an object of the present invention to produce an animal model for CHF and coronary atherosclerosis regression.

It is a further object of the present invention to use the CHF model to study the progression of CHF and test the effects of potential drugs and therapies to promote the growth of new blood vessels or heart muscle.

It is still another object of the invention to use the CHF model to screen for therapeutic compounds that could accelerate coronary atherosclerosis regression.

BRIEF SUMMARY OF THE INVENTION

An animal model has been developed where the animals can survive myocardial infarctions caused by diet-induced coronary atherosclerosis, and live with chronic heart failure. This animal model is a result of reduced activity of scavenger receptor class BI (SR-BI) and ApoE and the inducible activity of the Mx1-Cre gene. In a preferred embodiment, the model is a result of crossbreeding two transgenic mouse lines: a knockout of SR-BI (SRBI$^{-/-}$) and and impaired ApoE expressor (Apoe$^{h/h}$) to generate a strain referred to as Apoe$^{h/h}$ SRB1$^{-/-}$ mice, which is then crossbred to mice that carry the inducible Mx1-Cre transgene. These offspring can rapidly and permanently lower their high blood cholesterol levels caused by dietary challenge. The ability to rapidly and permanently lower blood cholesterol levels in these mice stops and may cause the regression of occlusive coronary atherosclerosis restoring blood flow to the heart, allowing the mice to survive from myocardial infarction and live with chronic heart failure.

As described in the example, Apoe$^{h/h}$SRB1$^{-/-}$ mice were bred to mice that carry the inducible Mx1-Cre transgene, resulting in Apoe$^{h/h}$SRB1$^{-/-}$Mx1-Cre mice that are sensitive to diet-induced coronary atherosclerosis and develop fatal myocardial infarctions within 35 days of dietary challenge. However, this new strain of mice can survive its heart attacks if switched to a normal low fat diet and given a single intraperitoneal injection of polyinosinic polycytidylic ribonucleic acid (pI-pC). This injection rapidly activates the Mx1-Cre gene that permanently restores normal Arg-61 ApoE levels in blood, which rapidly and permanently lowers blood cholesterol levels in a few days. Surviving Apoe$^{h/h}$SRB1$^{-/-}$Mx1-Cre mice can then live for many months. There is evidence of myocardial infarction and ventricular enlargement upon histological analysis of their heart.

This animal model can be used to study mechanisms and progression of CHF as a function of diet, screening of drugs for efficacy or undesirable side effects, and social environmental effects. This model can also be used to screen therapeutic agents for their ability to accelerate coronary atherosclerosis regression disorders, or having an effect on disorders selected from the group consisting of cardiac fibrosis, myocardial infarction, defects in electrical conductance, atherosclerosis, unstable plaque, heart failure, infertility, reduced life span, abnormal red blood cell development abnormal apolipoprotein metabolism stroke and diseases associated with abnormal cardiac structure or function or elevated cholesterol or lipoprotein levels. The studies demonstrate that animals which are deficient in SR-BI, hypomorphic for ApoE and posses the inducible Mx1-Cre gene, are not only excellent models for CHF but also coronary atherosclerosis regression since the animals can survive diet-induced heart attacks and histological analysis of their hearts shows evidence of myocardial infraction and ventricular enlargement. Consequently, the surviving Apoe$^{h/h}$SRB1$^{-/-}$Mx1-Cre mice are a unique murine model of chronic heart failure that simulates chronic heart failure in humans who survive heart attacks caused by coronary atherosclerosis.

DETAILED DESCRIPTION OF THE INVENTION

I. The Animal Model

Figure 1:
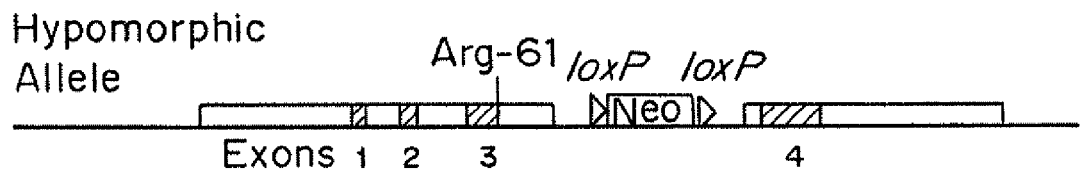
FIG. 1 is a schematic of the construct of the hypomorphic allele.

The preferred animal model for inducing chronic heart failure is an animal with reduced activity of both SR-BI and ApoE, and inducible activity of the Mx1-Cre gene or another inducible promoter.

Transgenic Animals

Preferably this animal model is a combination of SR-BI knockout (SRB1$^{-/-}$), hypoE (Apoe$^{h/h}$) and a mouse that carries the inducible Mx1-Cre gene, resulting in the Apoe$^{h/h}$ SRB1$^{-/-}$Mx1-Cre mouse. Heterozygous animals that can be bred to produce the homozygous animals are also described. The Apoe$^{h/h}$SRB1$^{-/-}$ mouse is defined as a transgenic mouse where the SR-BI gene is knocked out and the ApoE gene is inhibited to very low levels (~2-5-5%). The resulting Apoe$^{h/h}$ SRB1$^{-/-}$ then crossed with mice that carry the inducible Mx-1-Cre transgene.

SR-B1 Knockout Animals

Scavenger receptor class B, type I (SR-BI) is a receptor for high-density lipoprotein (HDL) that mediates cellular uptake of HDL cholesteryl ester (HDL CE) and cholesterol efflux and is the major route for cholesterol delivery to the steroidogenic pathway. SR-BI is a cell surface receptor for HDL and other lipoproteins (LDL and VLDL) and mediates the selective uptake of lipoprotein cholesterol by cells. SR-BI is localized in some cells in specialized microvillar channels in the plasma membrane that retain HDL and are sites of selective uptake of HDL CE. The formation of microvillar channels in the adrenal gland requires SR-BI and is regulated by adrenocorticotropin hormone. SR-BI-mediated uptake of HDL CE is a two-step process that requires high-affinity binding of HDL followed by transfer of CE to the membrane. CE uptake is followed by hydrolysis to free cholesterol by a neutral CE hydrolase. Studies of genetically manipulated strains of mice have established that SR-BI plays a key role in regulating lipoprotein metabolism and cholesterol transport to steroidogenic tissues and to the liver for biliary secretion. SR-BI knockout mice display elevated levels of plasma lipoprotein cholesterol.

In one embodiment, SR-BI knockout mice were made using pol2sneobpA and herpes simplex virus thymidine kinase (TK) cassettes in coding exon 1. Methods for producing this animal are described in U.S. Patent Application Publication No. US2002/0108131 to Krieger et al. These animals exhibit hypercholesterolemia (Rigotti et al (1997) *Proc Natl Acad Sci USA* 94, 12610-12615) with abnormally low biliary cholesterol excretion. These animals do not exhibit rapid spontaneous atherosclerosis on a standard low fat chow diet and have been reported to have a high unesterified cholesterol/total cholesterol (UC/TC) ratio (~0.5) (Van Eck et al (2003) *J Biol Chem* 278(26): 23699-23705; Braun et al (2003) *Proc Natl Acad Sci* 100:7283-7288).

HypoE Animals

Apolipoprotein E (ApoE) is an important structural and functional protein component of lipoproteins that plays a prominent role in lipid metabolism. As a high affinity ligand for the LDL receptor, ApoE mediates the uptake of plasma remnant lipoproteins by the liver (Mahley and Ji (1999) *J Lipid Res* 40:1-16; Cooper (1997) *J Lipid Res* 38:2173-2192). In humans, three common types of ApoE exist: ApoE2, ApoE3 and ApoE4 (Weisgraber (1994) *Adv Protein Chem* 45:249-302). Subtype ApoE4 in humans is characterized by arginine at positions 112 and 158 and the murine ApoE4 analog is characterized by an arginine at position 61 in the protein sequence and is associated with elevated plasma cholesterol and LDL levels and predisposes to cardiovascular disease (Raffai et al (2001) *Proc Natl Acad Sci* USA 98(20): 11587-11591). Unlike ApoE2 and ApoE3, ApoE4 associates preferentially with VLDL.

In one embodiment, a hypomorphic ApoE (Apoe$^{h/h}$) mouse is made by incorporating into the genome an Arg-61 allelic variant of mouse ApoE designed to resemble human ApoE4 (Raffai et al (2001) *Proc. Natl. Acad. Sci. USA* 98(20): 11587-11591) Methods for producing this animal are described in U.S. Patent Application Publication No. US2002/0194628 to Weisgraber et al. These animals express only approximately 5% of normal ApoE mRNA levels in all tissues and ApoE mRNA is barely detectable in tissues with normally low ApoE levels. Inherent variations exist between mice strains and therefore normal ApoE levels are defined as the ApoE levels observed in the wild type mouse strain used to generate the corresponding hypoE expressor. Insertion of a neo cassette flanked by loxP sites in the third intron of ApoE reduced expression of the Arg-61 allelic variant in ApoE mice and resulted in plasma ApoE levels that were approximately 2-5% of normal. Unlike other educed ApoE mice, Apoe$^{h/h}$ mice had a near normal lipoprotein cholesterol profile when fed a typical low fat chow diet. Total cholesterol and triglyceride levels were slightly higher than wild type (98 versus 65 mg/dl and 49 versus 26 mg/dl respectively). Levels of HDL were similar to wild type and most of the lipoprotein increases were seen in VLDL, IDL and LDL fractions. Apoe$^{h/h}$ mice were susceptible to high fat diet-induced hypercholesterolemia, which was fully reversed within 3 weeks after resumption of a chow diet (Raffai and Weisgraber (2002) *J. Biol Chem.* 277(13)11064-11068).

The SR-BI/hypoE Combination Animals

SRBI$^{-/-}$ and Apoe$^{h/h}$ animals can be crossbred to yield a combination mouse with both altered genes (Apoe$^{h/h}$ SRB1$^{-/-}$). The resulting Apoe$^{h/h}$SRB1$^{-/-}$ mouse has elevated ApoE expression after fasting for either 4 hours or overnight. The increase in ApoE expression is a result of the SR-BI knockout as ApoE levels are lower in wild type and Apoe$^{h/h}$ mice. Plasma lipids are markedly increased in Apoe$^{h/h}$ SRB1$^{-/-}$ mice specifically with respect to very low density lipoprotein (VLDL).

Animals with reduced SR-BI activity can be crossed with animals with reduced ApoE activity to give a feeding-dependent CHD. Other combinations can include PDZK1 knockout mice crossed with ApoE knockout mice or hypoE mice. Transgenic mice are available with each single altered gene and a combination transgenic can be obtained by crossbreeding the two lines. Resulting combination transgenic mice should have characteristics of both single transgenics.

MX1-CRE Mice

Somatically inducible Cre lines are used extensively to study gene function. Three transgenic mouse lines, two with Cre activity controlled at the transcriptional level (Ahcre, Mx1cre), and one controlled at the protein level (R26creER$^T$), were described by Kemp, et al. Nucleic Acids Res. 2004; 32(11): e92. See also Zhong-Min Guo, et al., Acta Biochimica et Biophysica Chimica 37(2):133 (February 2005).

Apoe$^{h/h}$SRB1$^{-/-}$Mx1-Cre is produced by breeding the SRBI ApoE deficient mice with MX1-CRE mice. Schneider, et al. Am. J. Physiol. Renal Physiol. 284(2):F411-F417 (2002) describes the Cre/loxP transgenic system and how it may be used to achieve temporally and/or spatially regulated gene deletion in a transgenic mouse. As described by Schneider, et al., the Mx1Cre mouse expresses Cre recombinase under control of the IFN-inducible Mx1 promoter. Mx1Cre mice were crossed with a reporter strain (ROSA26tm1Sor) in which beta-galactosidase activity is expressed only after Cre-mediated recombination to determine the cellular pattern of Cre-mediated genetic recombination in the kidney and other tissues. Widespread recombination was observed in vascular endothelium as well as in the liver and spleen. Recombination was restricted to subsets of stromal cells in uterus, duodenum, colon, aorta, and kidney. In the cortex, chi-galactosidase activity was detected in a subset of tubules and all glomerular cells, including endothelium, mesangium, and podocytes. No chi-galactosidase activity was detected in proximal tubules. Costaining of kidneys with segment-specific markers demonstrated induction of chi-galactosidase activity in collecting duct, with sporadic labeling of the thick ascending limb but no significant labeling of distal convoluted tubules. These results demonstrate that Mx1-driven gene recombination is spatially as well as temporally restricted.

This mouse is available from The Jackson Laboratory. The Cre recombinase is under the control of the Mx1 promoter. This promoter is silent in healthy mice, but can be induced to high levels of transcription by administration of interferon alpha, interferon beta, or synthetic double-stranded RNA. When combined with a mutant carrying a gene that has been flanked by loxP recognition sites, the expression of Cre recombinase causes the flanked gene to be removed. This provides researchers with the capability to induce the "knockout" at any time during development. There was ~1% background recombination seen in mice not treated with interferon. The percent deletion of the targeted gene varied depending on tissue type, presumably due to the amount of interferon-responsive cells present or to the availability of interferon in each organ. These mice were created using a transgenic construct containing the mouse Mx1 gene promoter, nuclear localization sequence-modified Cre recombinase and a 2.1 kb fragment from the human growth hormone gene was injected into (C57BL/6J×CBA/J)F2 fertilized eggs. The resulting transgenic mice were crossed to (C57BL/6J× 129Sv)F2 mice for an unknown number of generations. The mice were then backcrossed onto the C57BL/6J background for 7 generations.

This model can be developed in other species that normally express SR-B1 and ApoE using the general methods listed above to inhibit expression of appropriate SR-BI and ApoE species homologs. Examples of other species include but are not limited to non-human primates, rats, hamsters, rabbits, dogs, cats, cows, pigs, goats, and sheep. (See Clark and Whitelaw 2003 *Nat Rev Genet.* October 4(10):825-33).

Small Molecules

Other embodiments include using animals where SR-BI and/or ApoE activity is inhibited by administration of drugs or nucleic acids. SR-BI can be inhibited by small molecules such as BLTs (Nielands et al. 2002 *Proc Natl Acad Sci USA*, 99(24):15422-7) or by expressing an inhibitory transgene such as siRNA which is commonly used to inhibit gene expression (see Dorsett Y, Tuschl T. 2004 *Nat Rev Drug Discov.* April 3(4):318-29) or altering other genes that regulate SR-BI expression and activity such as PDZK1 (Kocher et al. 2003 *J Biol Chem* 278(52):52820-52825). Similarly, ApoE can be inhibited by siRNA and by small molecules and altering the expression of genes that regulate ApoE expression.

SR-BI can be inhibited directly or indirectly by administering small molecules such as BLTs (compounds that block lipid transport) (Nielands et al. 2002 *Proc Natl Acad Sci* USA. 99(24):15422-7) or other compounds or antibodies that may have blocking actions on SR-BI or proteins that regulate SR-BI activity. SR-BI activity can also be inhibited by expressing an inhibitory transgene such as siRNA which is commonly used to inhibit gene expression. (See Dorsett Y, Tuschl T., 2004 *Nat Rev Drug Discov*, April 3(4):318-29). Double-stranded RNA-mediated interference (RNAi) is a simple and rapid method of silencing gene expression in a range of organisms. The silencing of a gene is a consequence of degradation of RNA into short RNAs that activate ribonucleases to target homologous mRNA. The resulting phenotypes either are identical to those of genetic null mutants or resemble an allelic series of mutants. Similarly, ApoE can be inhibited by siRNA and by small molecules or antibodies in a similar manner. Altering the expression of genes that regulate ApoE expression is another method to reduce ApoE activity. Animals with reduced SR-BI activity can be crossed with animals with reduced ApoE activity to give a feeding-dependent CHD.

II. Methods of Making the Animal Model

Generation of Animals with Reduced SR-BI or ApoE Activity

With the knowledge of the sequence and or gene structure of the cDNA or genomic DNA encoding SR-BI, ApoE and regulatory sequences regulating expression thereof, it is possible to generate transgenic animals, especially rodents, with genotype of SR-BI$^{-/-}$/hypoE (Apoe$^{h/h}$SRB1$^{-/-}$). For example altering other genes that regulate SR-BI expression and activity such as PDZK1 (Kocher et al. 2003 *J Biol Chem*

278(52):52820-52825) also can inhibit SR-BI activity. Transgenic mice are separately generated for each altered gene and can be crossbred to obtain combination genotypes.

The SR-BI knockout animals are preferably made using techniques that result in "knocking out" of the gene for SR-BI. These animals are preferably made using a construct that includes complementary nucleotide sequence to the SR-BI gene, but does not encode functional SR-BI, and is most preferably used with embryonic stem cells to create chimeras. Animals which are heterozygous for the defective gene can also be obtained by breeding a homozygote normal with an animal which is defective in production of SR-BI. Methods are disclosed in U.S. Patent Application Publication No. 2002/0108131.

HypoE mice expressing reduced levels of ApoE can be generated by homologous recombination in embryonic stem cells. (Raffai et al. (2001) *Proc Natl Acad Sci U.S.A.* 98, 11587-11591). A neo cassette flanked by loxP sites was inserted into ApoE intron 3 to follow the replacement of the human equivalent of Thr-61 by an arginine. (Raffai and Weisgraber (2002) *J. Biol Chem.* 277(13)11064-11068). Correctly targeted embryonic stem cell clones were injected into blastocysts using standard microinjection techniques.

These manipulations can be performed by insertion of cDNA or genomic DNA into the embryo or embryonic stem cells using microinjection or other techniques known to those skilled in the art such as electroporation, as described below. Nuclear transfer techniques can also be used to transfer altered genetic material in generating transgenic animals. Alternatively SR-BI and ApoE encoding genes can e modified by homologous recombination with a DNA for a defective gene, such as one containing within the coding sequence an antibiotic marker, which can then be used for selection purposes.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats and can be extended to other species when analogous techniques are developed.

The procedures for manipulation of the embryo and for microinjection of DNA are described in detail in Hogan et al. Manipulating the mouse embryo, Cold Spring Harbor Laboratory, Cold Spring Harbor, N.Y. (1986). These techniques are readily applicable to embryos of other animal species, and, although the success rate is lower, it is considered to be a routine practice to those skilled in this art. Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987). Transfection is carried out by one of several methods described in detail in *Current Protocols in Molecular biology:* Ch. 9 *Introduction of DNA into Mammalian Cells*; John Wiley & Sons, New York, N.Y. ©2001). Once the transgenic animals are identified, lines are established by conventional breeding. Dual species crosses can be obtained by cross mating and breeding to homozygosity. Methods of breeding transgenic mice are routine in the art.

the SR-BI knockout and double knockouts can be crossed with other types of genetically modified animals (either naturally occurring mutations or genetically engineered animals). Many such animals are described in the literature and available from companies such as Jackson Laboratories, Bar Harbor, Me.

III. Method of Inducing CHF in Animal Model

Genetically engineered mice that express low amounts of Arg 61 apoE, called hypo E or ApoeR61$^{h/h}$ mice, were bred to mice that are deficient in a protein called Scavenger Receptor Class B, type 1, referred to as SRB1$^{-/-}$ mice. The resulting offspring of this experiment are designated as Apoe$^{h/h}$SRB1$^{-/-}$ mice. Apoe$^{h/h}$SRB1$^{-/-}$ mice have slightly elevated blood cholesterol levels when fed a normal low fat diet, but do not develop coronary atherosclerosis or heart disease. However, when fed a diet rich in fat and cholesterol, Apoe$^{h/h}$SRB1$^{-/-}$ mice develop very high blood cholesterol levels because of their low amounts of Arg61 apoE in the blood. High blood cholesterol levels rapidly cause occlusive coronary atherosclerosis in these mice, and they are subject to sudden death from severe heart failure caused by myocardial infarctions within 35 days of initiating the high cholesterol diet. Zhang, et al. Circulation 111(25) 3457-64 (2005).

The Apoe$^{h/h}$SRB1$^{-/-}$ mice have a life expectancy longer than a year when fed a normal low fat chow diet such as the RM3 diet containing 4.3% fat (Special diet services, Witham, UK). When fed a high fat, high cholesterol diet such as a Paigen or Paigen-type diet consisting of, for example, 7.5% cocoa butter, 15.8% fat, 1.25% cholesterol, and 0.5% sodium cholate, (ICN, Costa Mesa, Calif.; Research Diets, Inc., New Brunswick, N.J.), the mice develop severe hypercholesteremia. Such a diet causes atherosclerosis. Apoe$^{h/h}$SRB1$^{-/-}$ mice lose weight after a high fat feeding. Between 20 and 30 days of feeding the high-fat diet, survival of the SR-BI/hypoE mice goes from 100% to 50%, ultimately reaching 0% by approximately 45 days. Longevity depends in part of the number of animals per cage with animals maintained at only one mouse per cage exhibiting shorter survival times. The Apoe$^{h/h}$SRB1$^{-/-}$ mice display a dramatically increased heart weight compared to Apoe$^{h/h}$ mice similarly fed a high-fat diet. Heart to body ratio measurements for wt, SRB1$^{-/-}$ or Apoe$^{h/h}$ mice fed a high-fat diet are approximately 4 mg/g. The ratio for Apoe$^{h/h}$SRB1$^{-/-}$ mice is approximately 10 mg/g.

The induction of MI in this animal model is dependent on the type of diet. Not all high-fat diets are effective in inducing MI. Feed mixes with high cholesterol and no cholic acid such as the classic Western Diet consisting of approximately 20% fat and 0.2% total cholesterol do not work well to induce a rapid onset of CHD in the Apoe$^{h/h}$SRB1$^{-/-}$ mouse. Western Diets are available from Hope Farms, Woerden, The Netherlands, and Harlan Teklad, Madison, Wis.

The animal model was created by breeding Apoe$^{h/h}$SRB1$^{-/-}$ mice to mice that carry the inducible Mx1-Cre transgene, resulting in Apoe$^{h/h}$SRB1$^{-/-}$Mx1-Cre mice that are sensitive to diet-induced coronary atherosclerosis and develop fatal myocardial infarctions within 35 days of dietary challenge. However, this new strain of mice can survive its heart attacks if switched to a normal low fat diet and given a single intrapentoneal injection of polyinosinic polycytidylic ribonucleic acid (pI-pC). This injection rapidly activates the Mx1-Cre gene that permanently restores normal Arg-61 apoE levels in blood, which rapidly and permanently lowers blood cholesterol levels in a few days. Surviving Apoe$^{h/h}$SRB1$^{-/-}$MX1-Cre mice can then live for many months. Upon histological analysis of their heart, there is evidence of myocardial infarction and ventricular enlargement. Consequently, the surviving Apoe$^{h/h}$SRB1$^{-/-}$Mx1-Cre mice are a unique murine model of chronic heart failure that simulates chronic heart failure in humans who survive heart attacks caused by coronary atherosclerosis.

IV. Methods of Use in Research and Drug Screening

The animal model is highly unusual in being able to rapidly and permanently lower their high blood cholesterol levels caused by dietary challenge. The ability to rapidly and permanently lower blood cholesterol levels in these mice stops, and may cause the regression of, occlusive coronary atherosclerosis, restoring blood flow to the heart, allowing the mice to survive from myocardial infarction and live with chronic heart failure.

Chronic heart failure (CHF) is the most common medical condition afflicting the western world. The major cause of CHF is myocardial infarction, or the death of heart muscle during a heart attack, caused by coronary atherosclerosis. At the moment, there are very few technical solutions to significantly improve heart function in individuals with CHF. A major reason for the lack of treatments is the lack of reliable animal models that suffer from human-like CHF caused by myocardial infarction during a heart attack. This animal model that can recover from myocardial infarctions caused by the blockage of coronary arteries by atherosclerosis provides a unique platform for scientists to develop new treatments to reverse coronary atherosclerosis and treat chronic heart failure in humans.

For example, studies of the mouse model can be used to identify new classes of drugs or stem-cell based therapies to promote the growth of new blood vessels or heart muscle in the damaged part of the heart. Because the rapid lowering of blood cholesterol in the animal model likely promotes the regression of coronary atherosclerosis, companies could also use the animal model to screen for therapeutic compounds that could accelerate the regression of coronary atherosclerosis.

This animal model can be used to study mechanisms and progression of CHF as a function of diet, treatment with drugs to be screened for efficacy or undesirable side effects, and social environmental effects.

The studies described herein demonstrate that animals which are deficient in SR-BI and hypomorphic for ApoE and posses an inducible Mx1-Cre gene are not only excellent models for CHF since the animals develop myocardial infarction and ventricular enlargement characteristic of chronic heart failure in humans who survive heart attacks caused by coronary atherosclerosis, but are also models for atherosclerotic regression.

This animal can be induced with a high-fat, high cholesterol diet and given a single intrapentoneal injection of polyinosinic polycytidylic ribonucleic acid (pI-pC). This injection rapidly activates the Mx1-Cre gene that permanently restores normal Arg-61 apoE levels in blood, which rapidly and permanently lowers blood cholesterol levels in a few days. The animal model is then monitored at various time points until occurrence of heart attack. Animals can be studied using histology, electron microscopy, echocardiography, EKG, angiogram, and other diagnostic or imaging techniques. Differential gene expression during progression of CHD can be studied using DNA microarrays, differential display PCR or kinetic (real-time) PCR to identify candidate gene targets that change during onset of CHD. Proteomics and metabolomics can be used to assay for markers of disease in the blood, urine and other accessible tissues.

Compounds which prevent or alter progression of CHF or accelerate coronary atherosclerosis regression can be screened using this animal model as well as molecules that lower high cholesterol. The compound can be administered before, during or after the animal is fed a lipid enriched (high fat) diet. Symptoms of CHF progression can be monitored using diagnostic tests known in the art. Similarly, markers for CHF progression can be monitored by assaying blood, urine or any accessible fluid. Possible compounds to be screened include synthetic or organic small molecules, proteins, peptides, oligonucleotides, and gene drugs such as siRNA or nutraceuticals. Compounds can be administered singly or in combination with each other. The animal model can also be used to screen for which type of diet in combination with a compound is effective in preventing or altering progression of the disease.

Compounds are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compounds may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14, "Liposomes", *Drug Carriers in Biology and Medicine* pp. 287-341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The present invention will be further understood by reference to the following non-limiting examples.

EXAMPLE 1

Production and Characterization of Combination Transgenic Animals Which do not Express SR-BI and have Reduced ApoE Expression (Apoe$^{h/h}$)

Generation of Apoe$^{h/h}$SRB1$^{-/-}$ Mutant mice.

Apoe$^{h/h}$SRB1$^{-/-}$ mice were generated by crossbreeding established SR-BI knockout mice with hypoE mice. Homozygous SR-BI knockout dams are infertile (Miettinen et al. (2001) *J Clin Invest.* 108(11):1717-22; Rigotti et al (2003) *Endocr Rev.* 24(3):357-87). It is therefore necessary to use an SR-BI knockout male crossing with a hypoE dam while also accounting for the infertility of female mice during crossbreeding. Alternatively, the cholesterol lowering drug probucol has been shown to restore fertility in the SR-BI knockout females and may be administered during the breeding protocol (Miettinen et al. 2001).

Characterization of Plasma Lipids and Apolipoproteins

Plasma lipids and apolipoproteins were assayed for wild type and Apoe$^{h/h}$SRB1$^{-/-}$ mice and compared with hypoE, SR-BI−/− and ApoE−/− single knockout mice when fed a normal low fat, low cholesterol diet. These data are summarized in Table 1.

TABLE 1

Plasma lipids and apolipoprotein comparison on normal diet (mg/dl)

| | TC | FC | PL | TG | Ratio FC/TC | HDL |
|---|---|---|---|---|---|---|
| WT(n = 5) | 81 ± 31 | 19 ± 9 | 127 ± 40 | 40 ± 11 | 0.23 ± 0.04 | 52 ± 19 |
| SRBI$^{-/-}$ (n = 6) | 189 ± 46 | 92 ± 23 | 161 ± 34 | 38 ± 8 | 0.49 ± 0.02 | 125 ± 29 |
| Apoe$^{h/h}$ (n = 4) | 124 ± 16 | 30 ± 4 | 160 ± 38 | 36 ± 20 | 0.24 ± 0.02 | 83 ± 15 |
| ApoE −/− (n = 8) | 450 ± 63 | 147 ± 20 | 236 ± 19 | 48 ± 15 | 0.33 ± 0.04 | 33 ± 10 |
| Apoe$^{h/h}$SRB1$^{-/-}$ (n = 9) | 282 ± 25 | 173 ± 19 | 200 ± 17 | 47 ± 9 | 0.61 ± 0.06 | 148 ± 18 |

Abbreviations used: TC-Total cholesterol; FC-Free Cholesterol; PL-phospholipids; TG-triglycerides; HDL-high density lipoprotein, cholesteryl esters Animals were fed a high fat, high cholesterol, Paigen-type diet and plasma lipids and lipoproteins were similarly assayed. These results are summarized in Table 2.

TABLE 2

Plasma lipids and apolipoprotein comparison on high fat diet

| | TC | FC | PL | TG | Ratio FC/TC | HDL |
|---|---|---|---|---|---|---|
| WT(n = 10) | 214 ± 43 | 51 ± 12 | 168 ± 41 | 14 ± 7 | 0.24 ± 0.03 | 95 ± 21 |
| SRB1$^{-/-}$ (n = 5) | 693 ± 120 | 453 ± 75 | 408 ± 76 | 41 ± 10.5 | 0.65 ± 0.03 | 189 ± 52 |
| Apoe$^{h/h}$ (n = 8) | 1214 ± 224 | 277 ± 35 | 421 ± 41 | 34 ± 13 | 0.23 ± 0.04 | 18 ± 6 |
| ApoE−/− (n = 10) | 2731 ± 681 | 902 ± 325 | 857 ± 215 | 34 ± 8 | 0.32 ± 0.04 | 18 ± 6 |
| SR-BI/ApoE−/− | 970 ± 83 | 781 ± 65 | 678 ± 96 | 53 ± 16 | 0.806 ± 0.007 | |
| Apoe$^{h/h}$SRB1$^{-/-}$ (n = 6) | 1630 ± 337 | 1284 ± 274 | 976 ± 253 | 72 ± 13 | 0.79 ± 0.04 | 226 ± 36 |

Body weight was assessed in the various transgenic mice on normal and high fat Paigen-type diet. The Apoe$^{h/h}$SRB1 mouse was the only mouse that lost weight on the high fat diet. These data are summarized in Table 3.

TABLE 3

Body weight of transgenic mice strains

| Age | Wild Type | Apoe$^{h/h}$ | SR-BI$^{-/-}$ | Apoe$^{h/h}$SRB1$^{-/-}$ |
|---|---|---|---|---|
| 25 days | 13.0 g | 13.0 g | 13.3 g | 13.3 g |
| 60 days | 21.9 g | 22.3 g | 24.1 g | 23.0 g |
| 60 days (high fat for 28 days) | 24.7 g | 26.3 g | 27.5 g | 19.8 g |

Survival was assessed after the animals were administered a high-fat Paigen-type diet consisting of 7.5% cocoa butter, 15.8% fat, 1.25% cholesterol and 0.5% sodium cholate. Animals of various ages (3 weeks, 2 months and 6 months) were fed the high-fat diet and monitored for survival. For all age groups, mean survival time was approximately 30 days after commencement of the high-fat diet.

Heart weight was assessed for wild type, Apoe$^{h/h}$, SRB1$^{-/-}$ and Apoe$^{h/h}$SRB1$^{-/-}$ mice after being fed the high-fat diet. Wild type, Apoe$^{h/h}$ and SR-BI mice all exhibited a HBR of around 4 mg/g when fed a high fat diet while the Apoe$^{h/h}$SRB1 mouse exhibited a HBR of around 10 mg/g. Apoe$^{h/h}$SRB1 mice on a normal diet maintained an HBR around 4-5 mg/g.

Cardiac function was assessed in wild type, Apoe$^{h/h}$, SRB1$^{-/-}$ and Apoe$^{h/h}$SRB1$^{-/-}$ mice after being fed the high-fat diet using electrocardiography and echocardiography. Normal electrocardiography (ECG) patterns were seen in wild type, Apoe$^{h/h}$, and SRB1$^{-/-}$ mice while cardiac dysfunction was observed in Apoe$^{h/h}$SRB1$^{-/-}$ mice. Analysis using echocardiography, showed that Apoe$^{h/h}$SRB1$^{-/-}$ mice displayed increased heart wall thickness, increased LV (left ventricular) internal dimension at end systole (LVIDES), and reduced fractional shortening indicating contractile dysfunction. These data are summarized in Table 4. The electrocardiography and echocardiography results demonstrate that Apoe$^{h/h}$SRB1$^{-/-}$ mice fed a high-fat diet have impaired heart function.

TABLE 4

Echocardiographic analysis of mice on a high-fat diet which do not express SR-BI and have reduced ApoE expression (Apoe$^{h/h}$).

| | Apoe$^{h/h}$SRB1$^{-/-}$ normal diet (n = 6) | Apoe$^{h/h}$ high-fat diet (n = 6) | Apoe$^{h/h}$SRB1$^{-/-}$ high-fat diet (n = 9) |
|---|---|---|---|
| Heart Rate (bpm*) | 550 ± 23 | 539 ± 47 | 425 ± 27 |
| LVIDED (cm) | 0.31 ± 0.02 | 0.32 ± 0.01 | 0.32 ± 0.01 |
| LVIDES (cm) | 51 ± 2.3 | 59 ± 4.4 | 36 ± 2.3 |
| FS (%) | 51 ± 2.3 | 50 ± 4.4 | 36 ± 2.3 |
| PWT (cm) | 0.103 ± 0.005 | 0.102 ± 0.006 | 0.129 ± 0.009 |
| LV mass D3 (g) | 0.115 ± 0.008 | 0.115 ± 0.011 | 0.161 ± 0.017 |

*Values are mean ± SE.
Abbreviations used: bpm, beats per minute; LVIDED, left ventricular internal dimension (end diastole); LVIDES, left ventricular internal dimension (end systole); FS, fraction shortening; PWT, posterior wall thickness; LV mass, left ventricular mass.

EXAMPLE 2

Manipulation of the Progress of CHD by Feeding Mice Which do not Express SR-BI and Have Reduced ApoE Expression (Apoe$^{h/h}$) Different High Fat Diets Apoe$^{h/h}$SRB1$^{-/-}$ mice were generated as described in Example 1. 5 Apoe$^{h/h}$SRB1$^{-/-}$ mice were fed a normal low fat chow diet, a high fat (HF) diet consisting of 7.5% cocoa butter, 15.8% fat, 1.25% cholesterol, and 0.5% sodium cholate, a NCA diet consisting of 7.5% cocoa butter, 15.8% fat, and 1.25% cholesterol, or a Western Diet (WD) diet consisting of 21.2% fat, and 0.2% total cholesterol.

Plasma lipids and apolipoproteins were assayed for $Apoe^{h/h}$ $SRB1^{-/-}$ mice when fed a normal low fat, low cholesterol diet, the HF diet, the NCA diet, or the WD diet. These data are summarized in Table 5.

TABLE 5

Plasma lipid and apolipoprotein levels of SR-BI/hypo E mice on different high fat diets.

| Diet | TC | UC | PL | TG | Ratio UC/TC | UC + PL |
|---|---|---|---|---|---|---|
| Normal (n = 19) | 1010 ± 237 | 817 ± 188 | 686 ± 93 | 42 ± 18 | 0.811 ± 0.032 | 6.63 ± 1.7 |
| HF diet (n = 1) | 6630 ± 337 | 1,284 ± 274 | 976 ± 253 | 72 ± 13 | 0.787 ± 0.045 | 5.58 ± 1.5 |
| NCA diet (n = 14) | 918 ± 192 | 692 ± 168 | 608 ± 156 | 45 ± 24 | 0.751 ± 0.057 | 4.98 ± 1.4 |
| WD diet (n = 18) | 703 ± 131 | 496 ± 144 | 525 ± 145 | 61 ± 29 | 0.697 ± 0.104 | 4.22 ± 1.9 |

Abbreviations used: TC-Total cholesterol; UC-Unesterified Cholesterol; PL-phospholipids; TG-triglycerides.

Survival was assessed after the animals were administered a normal diet, a HF diet, a NCA diet, or a WD diet. Animals were fed the various diets and monitored for survival. Animals on the HF diet and the NCA diet died within seven weeks and fifteen weeks, respectively. Animals on the WD diet were not affected at 100 days. A 50% survival rate was observed at approximately 30 days for the high fat diet and approximately 60 days for the NCA diet.

Cardiac function was assessed in wild type, $Apoe^{h/h}$, $SRB1^{-/-}$ and $Apoe^{h/h}SRB1^{-/-}$ mice after being fed the high-fat diet using electrocardiography and echocardiography (Table 8). Normal electrocardiography (ECG) patterns were seen in wild type, $Apoe^{h/h}$, and $SRB1^{-/-}$ mice while cardiac dysfunction was observed in $Apoe^{h/h}SRB1^{-/-}$ mice. Following analysis using echocardiography, $Apoe^{h/h}SRB1^{-/-}$ mice displayed increased heart wall thickness, increased LV (left ventricular) internal dimension at end systole (LVIDES), and reduced fractional shortening indicating contractile dysfunction. These data are summarized in Table 6. The electrocardiography and echocardiography results demonstrate that $Apoe^{h/h}SRB1^{-/-}$ mice fed a high-fat diet have impaired heart function.

TABLE 6

Echocardiographic analysis of mice on a high-fat diet which do not express SR-BI and have reduced ApoE expression ($Apoe^{h/h}$).

| | $Apoe^{h/h}SRB1^{-/-}$ normal diet (n = 6) | $Apoe^{h/h}$ high-fat diet (n = 6) | $Apoe^{h/h}SRB1^{-/-}$ high-fat diet (n = 9) |
|---|---|---|---|
| Heart Rate (bpm*) | 550 ± 23 | 539 ± 47 | 425 ± 27 |
| LVIDED (cm) | 0.31 ± 0.02 | 0.32 ± 0.01 | 0.32 ± 0.01 |
| LVIDES (cm) | 51 ± 2.3 | 59 ± 4.4 | 36 ± 2.3 |
| FS (%) | 51 ± 2.3 | 50 ± 4.4 | 36 ± 2.3 |
| PWT (cm) | 0.103 ± 0.005 | 0.102 ± 0.006 | 0.129 ± 0.009 |
| LV mass D3 (g) | 0.115 ± 0.008 | 0.115 ± 0.011 | 0.161 ± 0.017 |

*Values are mean ± SE.
Abbreviations used: bpm, beats per minute; LVIDED, left ventricular internal dimension (end diastole); LVIDES, left ventricular internal dimension (end systole); FS, fraction shortening; PWT, posterior wall thickness; LV mass, left ventricular mass.

EXAMPLE 6

Production and Characterization of Combination Transgenic Animals Which do not Express the SR-B1 Gene, have Reduced ApoE Expression and Express the Inducible Mx-1-Cre Transgene ($Apoe^{h/h}SRB1^{-/-}$ Mx1-Cre Mice)

Generation of a Hypomorphic Allele of Apoe—A sequence replacement gene-targeting strategy was previously used to substitute arginine for the mouse equivalent of human Thr-61 as described by Raffai, et al. *Proc. Natl. Acad. Sci. U.S.A.* 98, 11587-11591 (2001). In creating an allelic variant of mouse Apoe designed to resemble human apolipoprotein E4 (apoE4), hypomorphic apoE (hypoE) mice that express only ~5% of normal apoE mRNA levels in all tissues were made by insertion of a neo cassette flanked by loxP sites in the third intron of Apoe. This reduced expression of the Arg-61 allelic variant in hypoE mice and resulted in plasma apoE levels that were ~2-5% of normal.

Breeding $Apoe^{neo+/neo+}$ Mice Expressing a Cre Transgene—$Apoe^{neo+/neo+}$ mice were crossed with inducible Mx1-Cre transgenic mice, as described by Raffai, et al. and Rohlmann, et al. *J. Clin. Invest.* 101, 689-695 (1998). Cre expression was induced in Mx1-Cre transgenic mice with a 250-μg intraperitoneal injection of pIpC (Sigma). Kühn, *Science* 269, 1427-1429 (1995). FIG. 1 is a schematic of the hyomorphic allele. The animals are characterized by 2-5% of wildtype plasma apoE levels, but display near normal plasma levels. Normal expression of apoE is restored by Cre-recombination in the Mx1-Cre mice.

Northern Blot Analysis of Total RNA—After extraction from several tissues and organs with Triazol reagent (Invitrogen), total RNA (~20 μg) was electrophoresed in a 1% agarose gel containing 20% formaldehyde, transferred by Hybond membrane (Amersham Biosciences), and hybridized to a mouse apoE cDNA probe labeled with [$^{32}$P]dCTP in Quickhyb solution (Stratagene, La Jolla, Calif.) at 65° C. overnight. The blot was washed in 0.3% standard sodium citrate (150 mM NaCl, 15 mM sodium citrate) and 0.1% SDS at 55° C. for 1 h and exposed to x-ray film overnight. A second blot of identical samples run on the same gel was hybridized with a mouse β-actin probe. Signals were quantified with a phosphor imager and quantification software (Bio-Rad QUANTITY ONE).

Lipid and Lipoprotein Determination—Lipids and lipoproteins were measured in 8-15-week old male mice that had been fasted for 4 h, anesthetized, and bled by retro-orbital puncture. Lipoproteins were fractionated by fast performance liquid chromatography (FPLC) on a Superose 6 column (Amersham Biosciences), and plasma was examined by agarose gel electrophoresis (Universal Gel/8, Helena Laboratories, Beaumont, Tex.). Cholesterol and triglyceride levels in plasma and FPLC fractions were determined with colorimetric assays (Spectrum (Abbott) and Triglycerides (Roche Molecular Biochemicals), respectively). Statistical analysis was performed with the nonparametric Mann-Whitney test.

ApoE and ApoB Quantitation—Fasted mouse plasma was subjected to SDS-PAGE with 10-20% or a 4-15% gels and transferred to nitrocellulose. Western blotting was performed with rabbit antisera against mouse apoE (Raffai) and apoB. Polyclonal antisera against mouse apoB100 and apoB48 were raised using mouse LDL (d=1.006-1.063 g/ml) isolated from Ldlr$^{-/-}$ mouse plasma by sequential density ultracentrifugation. New Zealand White rabbits were immunized with 100 μg of purified mouse LDL emulsified in complete Freund's adjuvant. Rabbits were boosted twice with antigen emulsified in incomplete Freund's adjuvant.

Western blots were incubated with primary antibodies at a dilution of 1:5000, and bound primary antibody was detected by a horseradish peroxidase-conjugated anti-rabbit antibody (Invitrogen). Signals were generated by incubating membranes with chemiluminescent reagent (Amersham Biosciences) and exposing them to x-ray film (Eastman Kodak Co.). Signals were quantified with a phosphor imager and quantification software (Bio-Rad QUANTITY ONE).

Diet-Induced Hypercholesterolemia—To induce hypercholesterolemia, mice were fed a high fat Western diet (21% fat, 0.12% cholesterol) (Harlan Teklad, Madison, Wis.) or the Paigen diet (16% fat, 1.25% cholesterol, 0.5% cholic acid) (ICN, Costa Mesa, Calif.) for 3 weeks. Unlike other mouse models with low levels of circulating apoE, hypoE mice had a nearly normal lipoprotein cholesterol profile when fed a chow diet. Further reduction of apoE expression in hypoE/Apoe$^{-/-}$ heterozygous mice led to an increase in remnant lipoprotein-associated cholesterol levels, demonstrating that hypoE mice express close to the threshold level of Arg-61 apoE required for a normal lipoprotein profile. Unlike wild type mice, hypoE mice were susceptible to diet-induced hypercholesterolemia, which was fully reversed within 3 weeks after resumption of a chow diet.

In Mx1-Cre transgenic hypoE mice, plasma apoE levels returned to normal within 10 days after gene repair and removal of the neo cassette following induction of Cre recombinase. HypoE mice provide the opportunity for conditional gene repair by crossing with inducible or lineage/cell type-specific Cre transgenic mice, generating new models to dissect the roles of apoE in atherosclerosis regression, immunoregulation, and neurodegeneration. Chimeric mice harboring a mutant Apoe allele, Apoe$^{neo+}$, in which intron 3 contained a neo cassette flanked by loxP sites, were crossed with C57BL/6 female mice to generate Apoe$^{neo+/WT}$ mice. These heterozygous mice were intercrossed to generate Apoe$^{neo+/neo+}$ mice. The mice were weaned at 21 days of age and housed in a barrier facility with a 12-h light/12-h dark cycle. Unless otherwise noted, they were fed a chow diet containing 4.5% fat (Ralston Purina, St. Louis, Mo.).

EXAMPLE 7

Induction of CHF in Apoe$^{h/h}$SRB1$^{-/-}$Mx1-Cre Mice

Production of Apoe$^{h/h}$SRB1$^{-/-}$Mx1-Cre Mice—To produce these mice, the Apoe$^{h/h}$Mx1-Cre mice were bred with heterozygote or homozygote SRB1$^{-/-}$ mice.

10 Apoe$^{h/h}$SRB1$^{-/-}$Mx1-Cre mice were fed a high cholesterol diet for 30 days. On day 31, they were injected with pI-pC, and then switched to a low fat diet. Of the 10 mice, 6 survived for two months. At that time point, their hearts were harvested and heart function was assessed in 4 of the 6 mice by Langendorf hemodynamic measurements.

Figure 2:
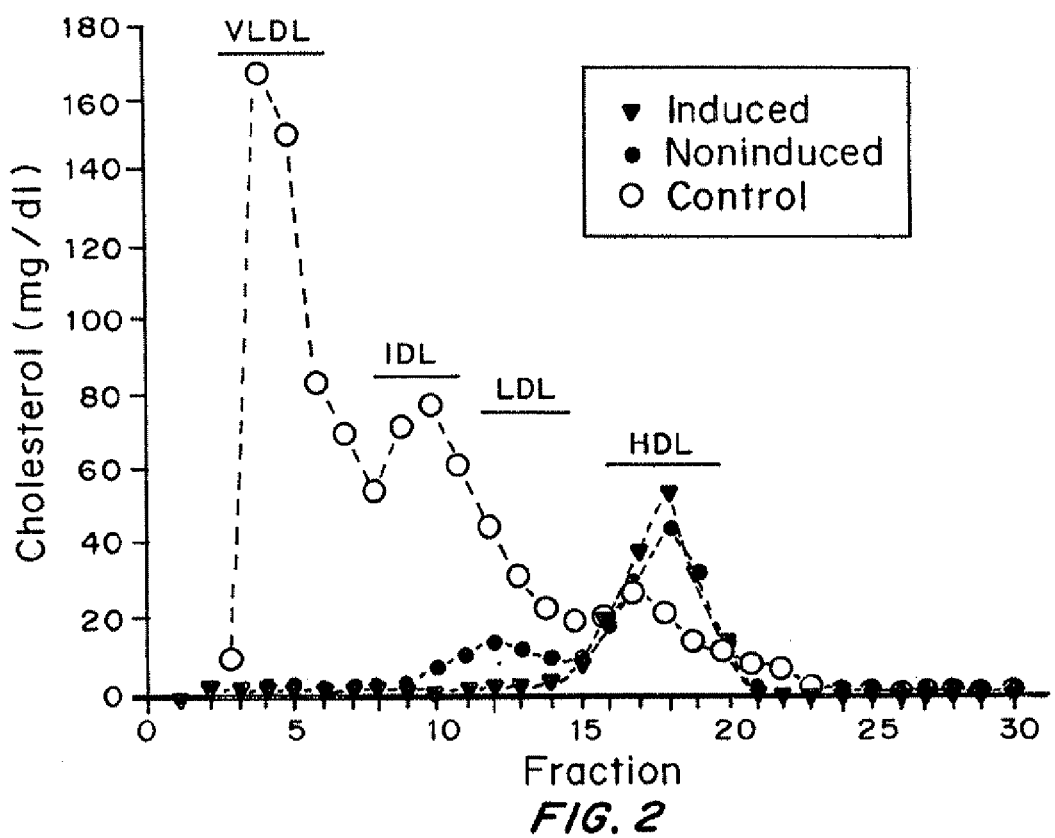
FIG. 2 is a graph of the cholesterol (mg/dl) versus fraction (VLDL), (IDL), (LDL), and (HDL), for induced (dark triangles), noninduced (dark circles), and control (open circles) Mx1-Cre hyopE mice.

FIG. 2 is a graph of the cholesterol (mg/dl) versus fraction (VLDL), (IDL), (LDL), and (HDL), for induced, noninduced, and control Mx1-Cre hypoE mice. The induced mice have very elevated HDL but low levels of VLDL, IDL and LDL.

Figure 3:
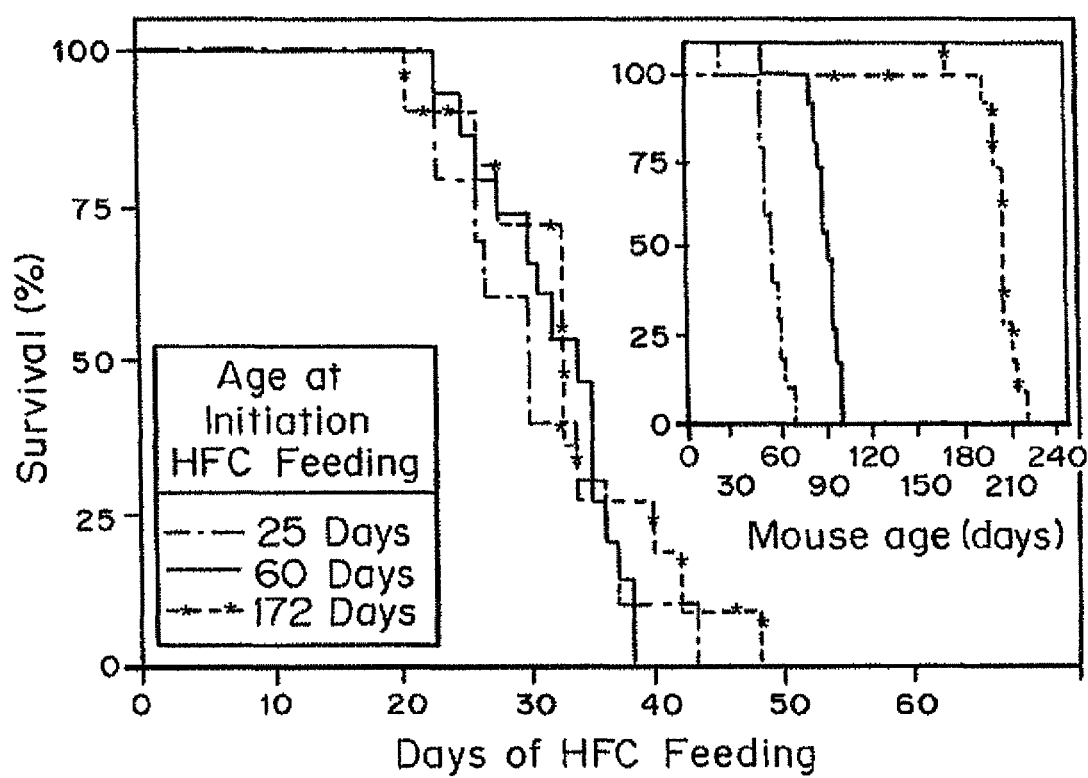
FIG. 3 is a graph of survival (%) versus days of HFC feeding as a function of age at initiation of feeding (broken line (no asterisk), 25 days; heavy line, 60 days; or broken line with asterisk, 172 days) and FIG. 3 insert, survival (%) as a function of mouse age (days).

FIG. 3 is a graph of survival (%) versus days of HFC feeding as a function of age at initiation of feeding (thin line, 25 days; heavy line, 60 days; or grey line, 172 days) and FIG. 3 insert, survival (%) as a function of mouse age (days). The results show that the younger the animals were fed the high cholesterol diet, the sooner they died.

The data revealed that all 4 mice had approximately 60% normal heart function. Next, histological analysis was performed on the hearts of the surviving mice. The data revealed evidence of multiple myocardial infarctions and enlarged ventricles, a pathological feature that is typical of chronic heart failure in humans who have suffered from a heart attack caused by coronary atherosclerosis.

Collectively, the data demonstrates that the engineered mice can live with chronic heart failure.

Those skilled in the art will recognize, or be able to ascertain using no more than routine experimentation, many equivalents to the specific embodiments of the invention described herein. Such equivalents are intended to be encompassed by the following claims.

We claim:
1. A transgenic mouse whose genome comprises:
   (a) a homozygous disruption of the endogenous Scavenger Receptor class B, type I gene (SR-B1$^{-/-}$);
   (b) a homozygous Arg-61 allelic variant of mouse apolipoprotein E gene (ApoE$^{h/h}$) having inserted at each allele a floxed neomycin cassette; and
   (c) an inducible Mx1-Cre transgene,
   wherein feeding the mouse a cholesterol enriched diet results in the induction of myocardial infarction and wherein following said myocardial infarction, normal ApoE levels can be restored by spatially and temporally regulating expression of the ApoE gene by inducing the Mx1-Cre gene and allowing the transgenic mouse to rapidly reduce its blood cholesterol and live with chronic heart failure while displaying myocardial infarctions and enlarged ventricles.

2. The transgenic mouse of claim 1, wherein the mouse is sensitive to diet-induced coronary atherosclerosis and develops fatal myocardial infarctions within 35 days of initiating a high cholesterol diet prior to said induction of Mx1-Cre.

3. A method for screening a compound for having an effect on disorders selected from the group consisting of atherosclerosis, and chronic heart failure comprising
   (a) administering a compound that may have an effect on chronic heart failure or arthrosclerosis to the transgenic mouse of claim 1 exhibiting chronic heart failure with myocardial infarctions and enlarged ventricles, and (b) determining the effect of the compound on said disorder in the mouse relative to a control mouse not treated with the compound.

4. A method for making the mouse of claim 1 for screening for compounds affecting the symptoms of a disorder selected from the group consisting of cardiac atherosclerosis and chronic heart failure, said method comprising
(a) crossing a transgenic mouse whose genome comprises a homozygous Arg-61 allelic variant of mouse ApoE (ApoE$^{h/h}$) gene having inserted at each allele a floxed neomycin cassette with a transgenic mouse whose genome comprises an inducible Mx1-Cre transgene to produce a ApoE$^{h/h}$/Mx1-Cre mouse;
(b) crossing a transgenic mouse whose genome comprises a homozygous disruption of the endogenous SR-B1 gene (SR-B1$^{-/-}$) with the ApoE$^{h/h}$/Mx1-Cre mouse to produce an ApoE$^{h/h}$/SR-B1$^{-/-}$Mx1-Cre mouse,
wherein feeding the transgenic ApoE$^{h/h}$/SR-B1$^{-/-}$Mx1-Cre mouse a cholesterol enriched diet results in the induction of myocardial infarction and wherein following said myocardial infarction, normal ApoE levels can be restored by spatially and temporally regulating expression of the ApoE gene by inducing the Mx1-Cre gene and allowing the transgenic mouse to rapidly reduce its blood cholesterol and live with chronic heart failure while displaying myocardial infarctions and enlarged ventricles.

* * * * *